United States Patent [19]

Pope et al.

[11] Patent Number: 5,359,541
[45] Date of Patent: Oct. 25, 1994

[54] FLUID DENSITY AND CONCENTRATION MEASUREMENT USING NONINVASIVE IN SITU ULTRASONIC RESONANCE INTERFEROMETRY

[75] Inventors: Noah G. Pope, Los Alamos; Douglas K. Veirs, Espanola; Thomas N. Claytor, Los Alamos, all of N. Mex.

[73] Assignee: The Regents of the University of California, Office of Technology Transfer, Alameda, Calif.

[21] Appl. No.: 24,128

[22] Filed: Mar. 1, 1993

[51] Int. Cl.$^5$ ............................................. G06F 15/20
[52] U.S. Cl. .................................. 364/497; 73/32 A; 364/550; 364/558
[58] Field of Search .............. 364/496, 497, 550, 558; 367/13; 73/32 A

[56] References Cited

U.S. PATENT DOCUMENTS

| | | | |
|---|---|---|---|
| 4,249,422 | 2/1981 | Gaunaurd et al. | 73/589 |
| 4,509,372 | 4/1985 | Mount | 73/861.28 |
| 4,618,769 | 10/1986 | Johnson et al. | 250/338 |
| 4,641,973 | 2/1987 | Nestler et al. | 356/418 |
| 5,062,296 | 11/1991 | Migliori | 73/579 |
| 5,078,011 | 1/1992 | Morkun et al. | 73/32 A |

OTHER PUBLICATIONS

Pope: "Solution Density and Concentration Measurement Using Noninvasive In Situ Ultrasonic Resonance Interferometry" LA-12352-T Thesis UC-711 and UC-706 Los Alamos Nation Laboratory Jul. 1992.
Gooberman; "Ultrasonics Theory and Application"; The English University Press Ltd.; 1969 pp. 146-150.
J. Dion et al., "Practical Ultrasonic Spectrometric Measurement of Solution Concentrations by a Tracking Technique," 37 IEEE Trans. Ultrason., Ferroelectrics, and Freq. Con., No. 2, pp. 190-195 (May 1990).
A. Loomis et al., "A Sonic Interferometer for Measuring Compressional Velocities in Liquids: A Precise Method," 17 J. Opt. Soc. Am., pp. 295-307 (1928).

*Primary Examiner*—Edward R. Cosimano
*Attorney, Agent, or Firm*—Ray G. Wilson

[57] ABSTRACT

The specific gravity or solute concentration of a process fluid solution located in a selected structure is determined by obtaining a resonance response spectrum of the fluid/structure over a range of frequencies that are outside the response of the structure itself. A fast fourier transform (FFT) of the resonance response spectrum is performed to form a set of FFT values. A peak value for the FFT values is determined, e.g., by curve fitting, to output a process parameter that is functionally related to the specific gravity and solute concentration of the process fluid solution. Calibration curves are required to correlate the peak FFT value over the range of expected specific gravities and solute concentrations in the selected structure.

2 Claims, 7 Drawing Sheets ns. 5,359,541

FLUID DENSITY AND CONCENTRATION MEASUREMENT USING NONINVASIVE IN SITU ULTRASONIC RESONANCE INTERFEROMETRY

This invention relates to the measurement of fluid characteristics and, more particularly, to fluid density and solute concentration measurement using noninvasive ultrasonic resonance interferometry. This invention was made with government support under Contract No. W-7405-ENG-36 awarded by the U.S. Department of Energy. The Government has certain rights in the invention.

BACKGROUND OF INVENTION

There are many applications where it is desirable to determine various characteristics of a fluid, such as the concentration of material in a fluid solution or the density of a fluid solution, where the measurement technique is noninvasive and does not expose workers to toxic fumes or spills, radioactive contamination and the like. There are existing methods that use sonic and ultrasonic excitation to measure sound velocity and concomitant solution density and/or solute concentration. The known techniques rely on the formation of standing waves in a liquid and are generally referred to as acoustic or ultrasonic interferometers. As noted by A. L. Loomis et al., "A Sonic Interferometer for Measuring Compressional Velocities in Liquids: A Precise Method," 17 J. Opt. Soc. Am., pp. 295–307 (1928), ultrasonic frequencies are preferred where the wavelength in the fluid is small compared with the diameter of the liquid column so that the sound velocity in the fluid is highly independent of the dimensions and the material of the vessel containing the fluid.

Typically, the instruments that measure the sound velocity use special sampling cells adapted to a particular technique and require that the excitation devices be suspended in the fluid. One particular device, described in G. L. Gooberman, *Ultrasonics Theory and Applications*, pp. 146–150, The English Universities Press, Ltd., London, United Kingdom (1968), provided a fixed-position transducer and a variable reflector in a liquid medium. The frequency of the transducer output was varied and its impedance was measured. The impedance measurement underwent minima and maxima, i.e., resonances, as the frequency was varied because of the force established by the standing wave pattern. Thus, frequencies for maximum impedance were measured and the frequency difference between adjacent maxima was related to the sound velocity in the liquid. The sound velocity was then related to fluid density and/or solute concentration in the fluid.

For a production method and apparatus, it would be desirable to provide a noninvasive technique that uses the fluid container walls as the interferometer. Accordingly, it is an object of the present invention to provide transducers external to a fluid container containing the fluid to be measured.

It is another object of the present invention to provide for measuring fluid characteristics without exposing workers to the fluid.

Yet another object of the present invention is to provide a measurement instrument that can be readily adapted to process pipes and storage vessels.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the subject of this invention may comprise a method for the determination of the specific gravity or solute concentration of a process fluid solution located in a selected structure. An excitation transducer and a receiver transducer are attached externally to the structure in operable proximity to the process fluid solution. The fluid solution and the structure are excited over a selected range of frequencies greater than response frequencies of the structure to generate an ultrasonic response spectrum for the fluid solution. A fast fourier transform (FFT) is then performed on the response spectrum to output a set of FFT values. A peak value of the FFT values is determined and output as a process value functionally related to the specific gravity or the solute concentration of the process fluid solution.

BRIEF DESCRIPTION OF THE DRAWINGS

The accompanying drawings, which are incorporated in and form a part of the specification, illustrate embodiments of the present invention and, together with the description, serve to explain the principles of the invention. In the drawings.

DETAILED DESCRIPTION OF THE INVENTION

A method for noninvasively measuring the density and/or solute concentration of fluids within a processing structure, e.g., a pipe or slab tank, uses ultrasonic resonance frequencies to develop a spectrum from which the density and solute concentration can be quantitatively determined. Transmitter and receiver transducers are located on the outside of a selected structure containing the fluid to be measured and a resonance frequency spectrum is determined. As shown herein, a fast fourier transform (FFT) of the spectrum provides a representative value of the spectrum that is directly related to fluid density and solute concentration.

Figure 1:
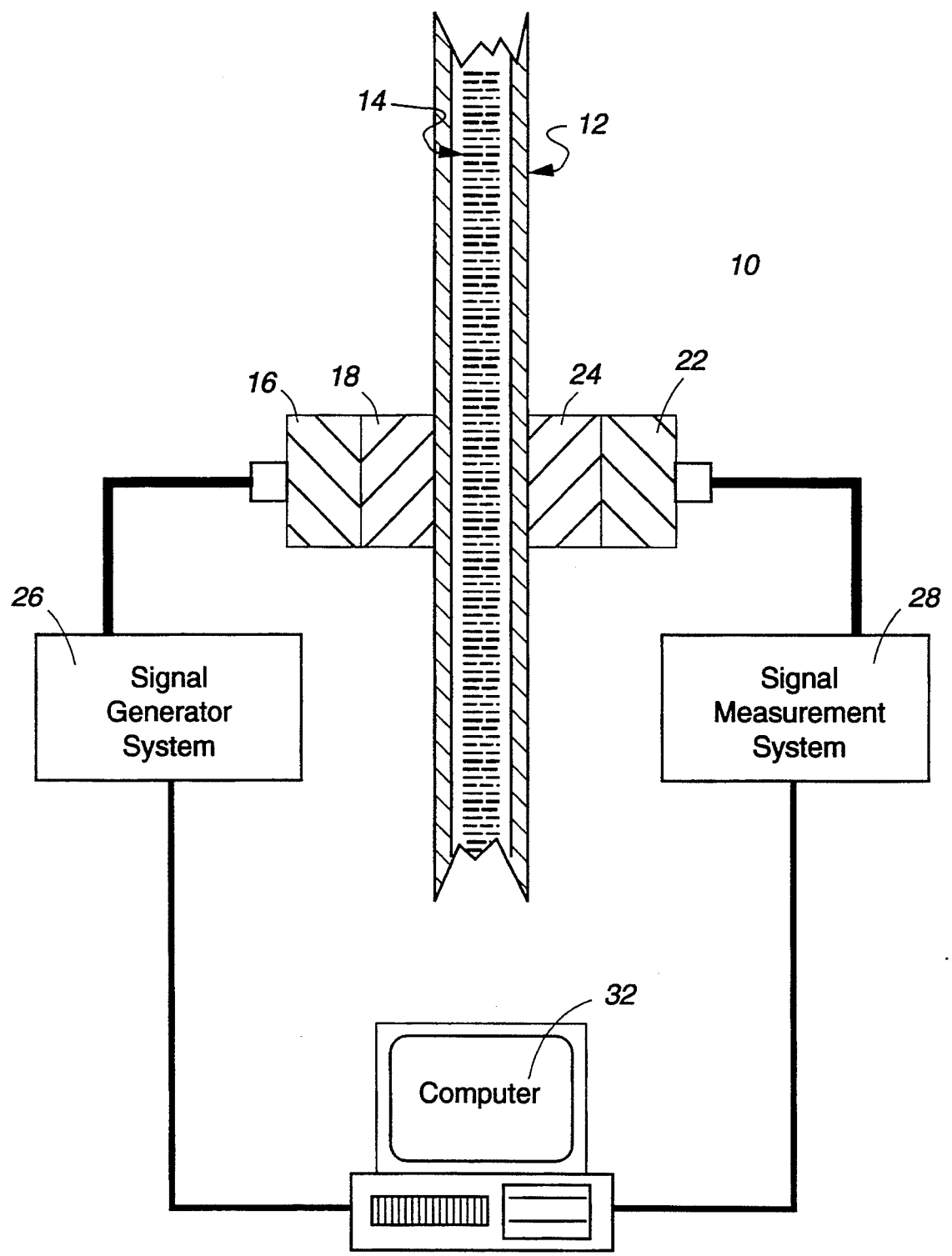
FIG. 1 is a pictorial illustration in block diagram form of an ultrasonic resonance measurement system according to one embodiment of the present invention.

Referring now to FIG. 1, ultrasonic measurement system 10 is pictorially illustrated in partial block diagram form. Ultrasonic transmitter 16 and receiver 22 transducers are coupled through acoustic couplers 18 and 24, respectively, to an external surface of a selected structure 12, typically a pipe or a tank, containing a fluid 14, which may be a solution whose specific gravity and/or solute concentration are to be measured. In one embodiment, transducers 16 and 22 are piezoelectric transducers (Babcock and Wilcox Model FC500) that are mounted on couplers 18 and 24, which are shaped to match the contour of structure 12 on one side and transducers 16 and 22 on the other side for efficiently transferring energy between the transducers.

Signal generator system 26 (e.g., Phillips Model PM5193 Synthesizer/Function Generator) provides a continuous sine wave output that may be swept over a suitable frequency range for energizing transmitter 16. Receiver 22 detects transmitted acoustic energy for input to signal measurement system 28. Signal measurement system 28 may include an amplifier (Analog Modules Model 323-1) and a peak sense and hold circuit (Analog Modules Model 610-2-20-50) for holding a peak output until the system is interrogated.

Computer 32 (e.g., Compaq 386 using a Metrabyte Model DAS-8 input board) controls data acquisition and analysis. As the excitation signal is swept through a range of frequencies, the structure/fluid system will encounter numerous resonances so that the output from signal measurement system 28 will be a pattern of maxima and minima voltage responses that are stored for processing in computer 32. It has been found that at frequencies greater than the resonance frequencies associated with the structure, the periodicity of the resonance peaks appears to be related only to the structure internal dimension and acoustic properties of the fluid solution. In other words, a resonance spectrum is obtained that is formed from the resonance frequency of the solution and its boundaries and harmonics of the resonance frequency. Thus, complex resonances associated with low frequencies are avoided. For example, for $\frac{3}{4}$ inch diameter stainless steel pipe, frequencies greater than 300 kHz appear to generate the desired correlation between resonance frequencies and solution specific gravity.

For solutions, the sound velocity is a function of composition and temperature. For instance, in aqueous salt solutions, the velocity increases with concentration and, hence, the interval between resonance peaks increases. For measurements over a selected frequency range, the present invention recognizes that the total number of resonance peaks will decrease with increasing concentration. Monitoring the total number of resonance peaks over a constant frequency range allows changes in the concentration of the enclosed salt solution to be monitored.

In one embodiment of the present invention, the total number of frequency peaks over the selected excitation frequency range is conveniently determined by FFT's. The measured resonance frequency spectrum contains frequency data and the FFT converts the frequency data to the time domain. The centroid of the peak in the FFT corresponds to the number of resonance peaks over the resonance spectrum.

Figure 2:
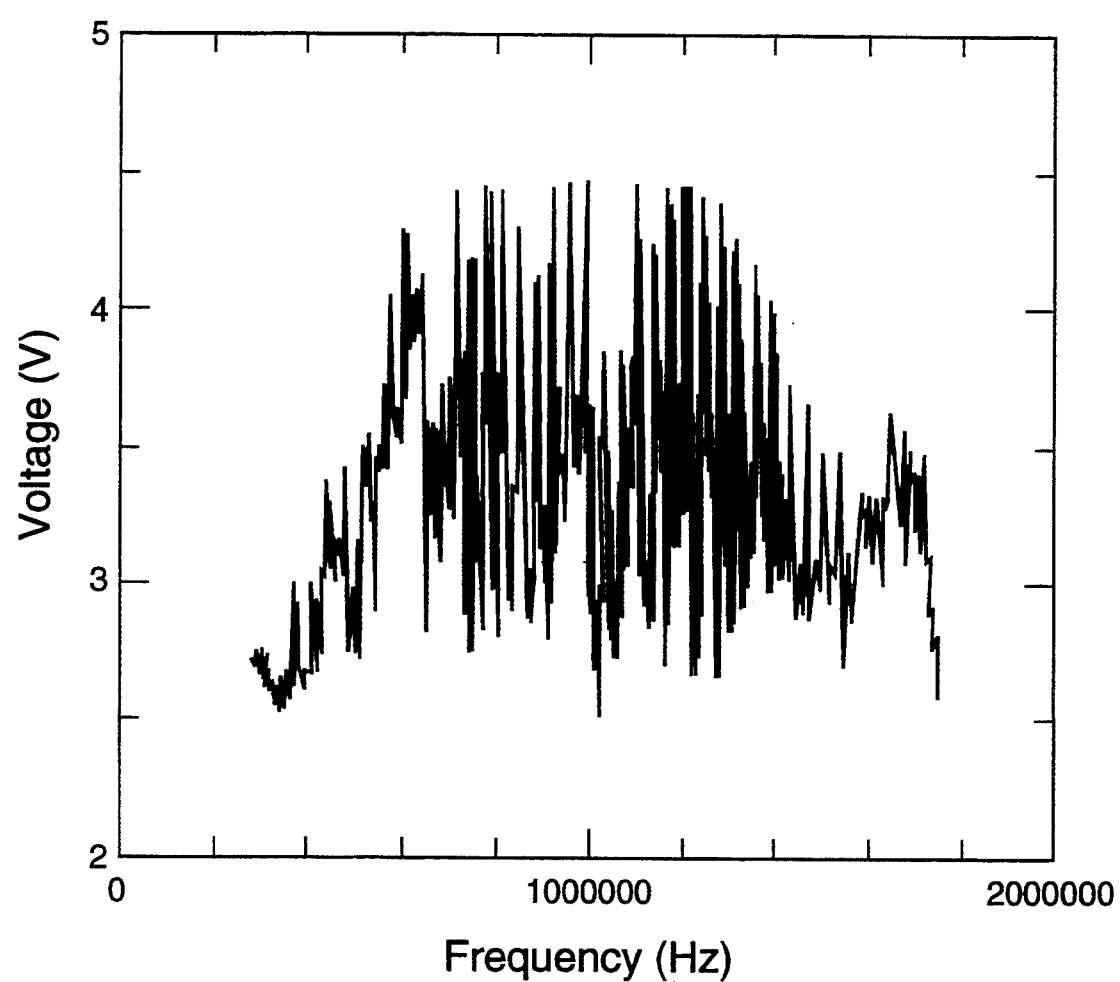
FIG. 2 graphically depicts a typical ultrasonic resonance spectrum for a container/solution system using the system shown in FIG. 1 where the container is a pipe.
Figure 3:
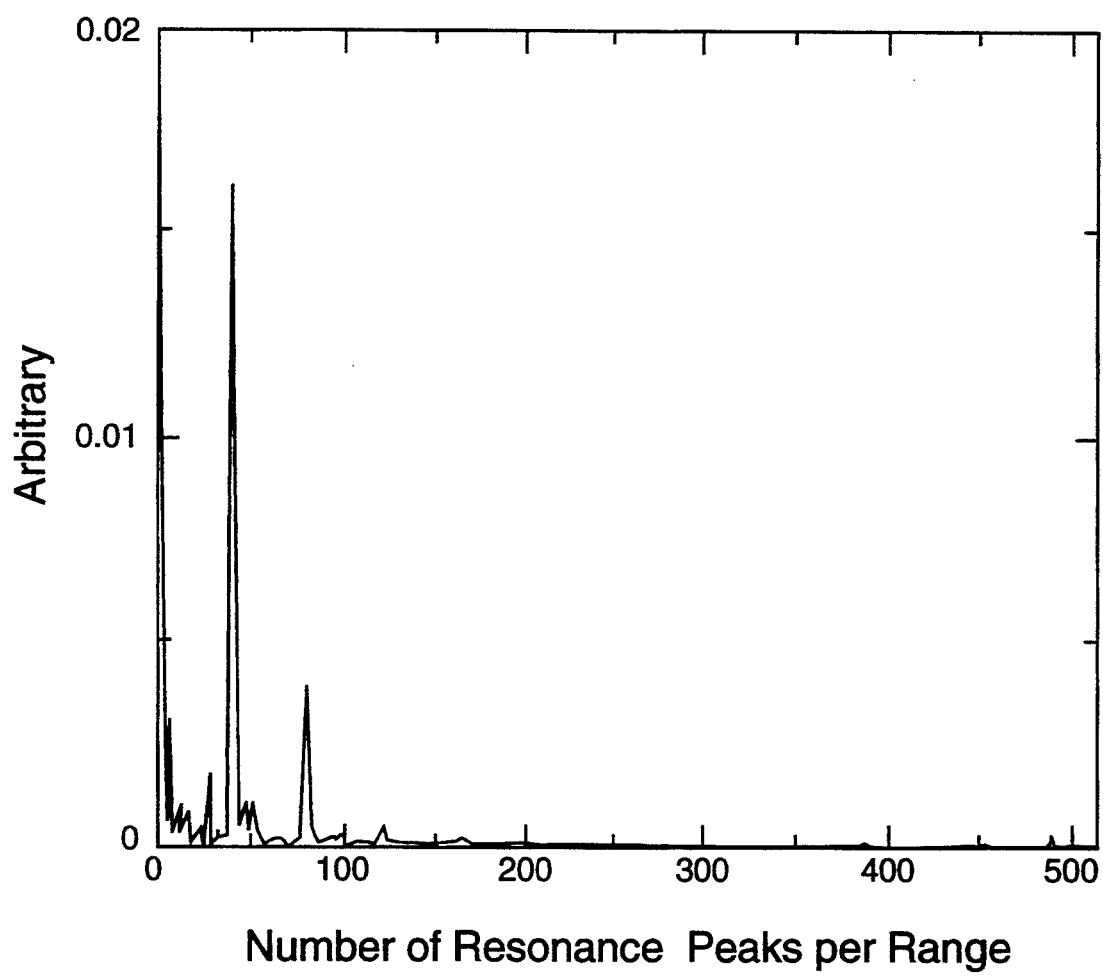
FIG. 3 graphically depicts the FFT spectrum of the resonance spectrum shown in FIG. 2.

FIG. 2 graphically depicts the resonance spectrum of a distilled water sample contained within a $\frac{3}{4}$ inch stainless steel pipe. It will be appreciated that the resonance peaks occur at regular and predictable intervals i.e., the primary resonance frequency. The FFT spectrum of the frequency spectrum shown in FIG. 2 is shown in FIG. 3. The frequency range shown in FIGS. 2 and 3 was from about 0.3 MHz to 1.8 MHz and was selected based on both empirical results and the frequency response of the transducers. A data set of 1024 measurements over that range was obtained. The FFT of the 1024 point data set resulted in a data set of 512 points. The number of resonance peaks over the frequency range is represented by the position of the largest peak in the FFT spectrum.

Since the FFT shown in FIG. 3 places the peak in an integer-valued channel between 1 and 512, the FFT can only resolve the position to the nearest integer. To increase the resolution, a Lorentzian curve fit was performed using Peakfit Software (Jandel Scientific, Inc.) on the FFT data to yield a real-valued FFT peak centroid. This value was used in a linear fit between solution specific gravity (SG) and the value (real, not integer) of resonance peaks over the range. To obtain the calibration and test data shown in FIGS. 4 and 5 and in Table A, a solution was used with distilled water as the solvent and salt (NaCl) as the solute. As the salt concentration in solution increased, the resonance period increased, which resulted in a decrease in the number of resonance peaks over that range. This decrease resulted in a shift or decreased value in the position of the primary peak in the FFT spectrum.

Figure 4:
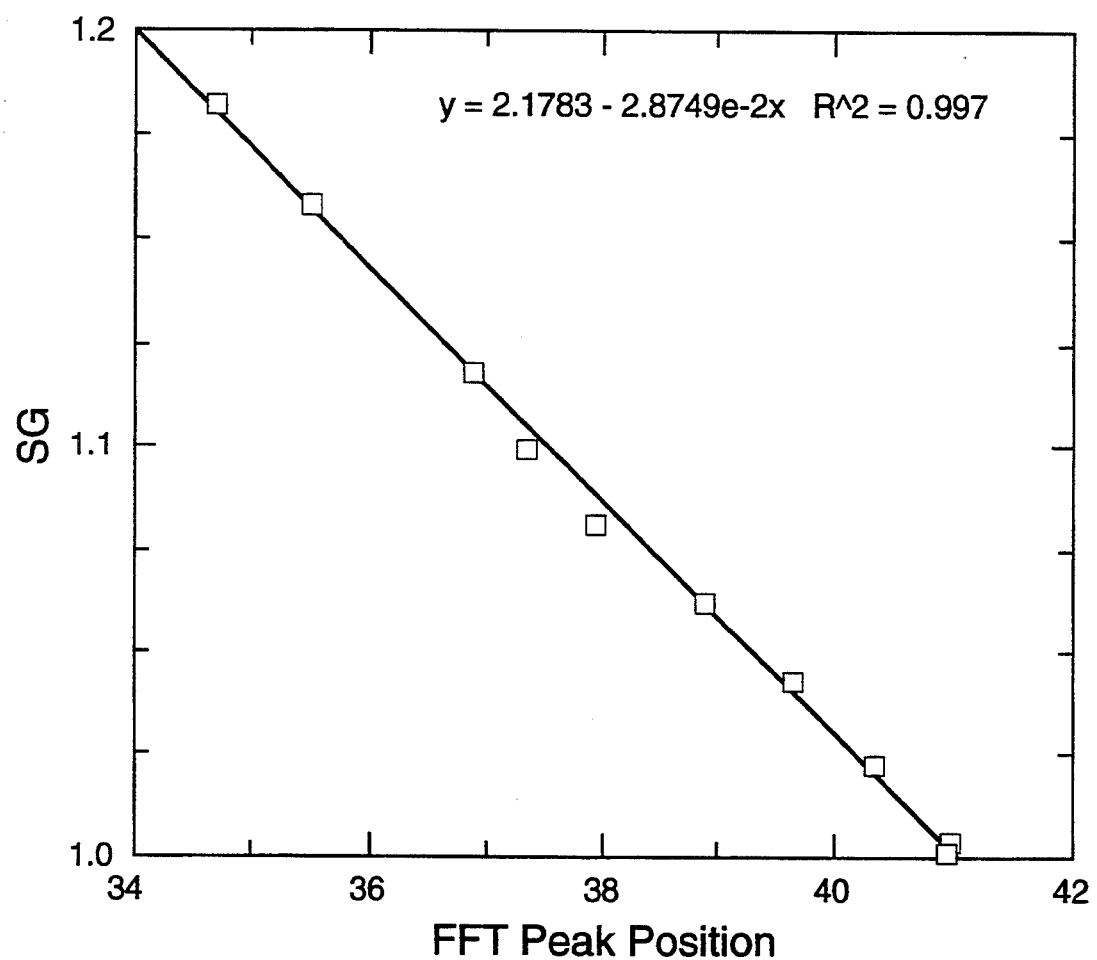
FIG. 4 graphically depicts a calibration curve of specific gravity (SG) for a NaCl-distilled water solution in a pipe as a function of the FFT peak value.
Figure 5:
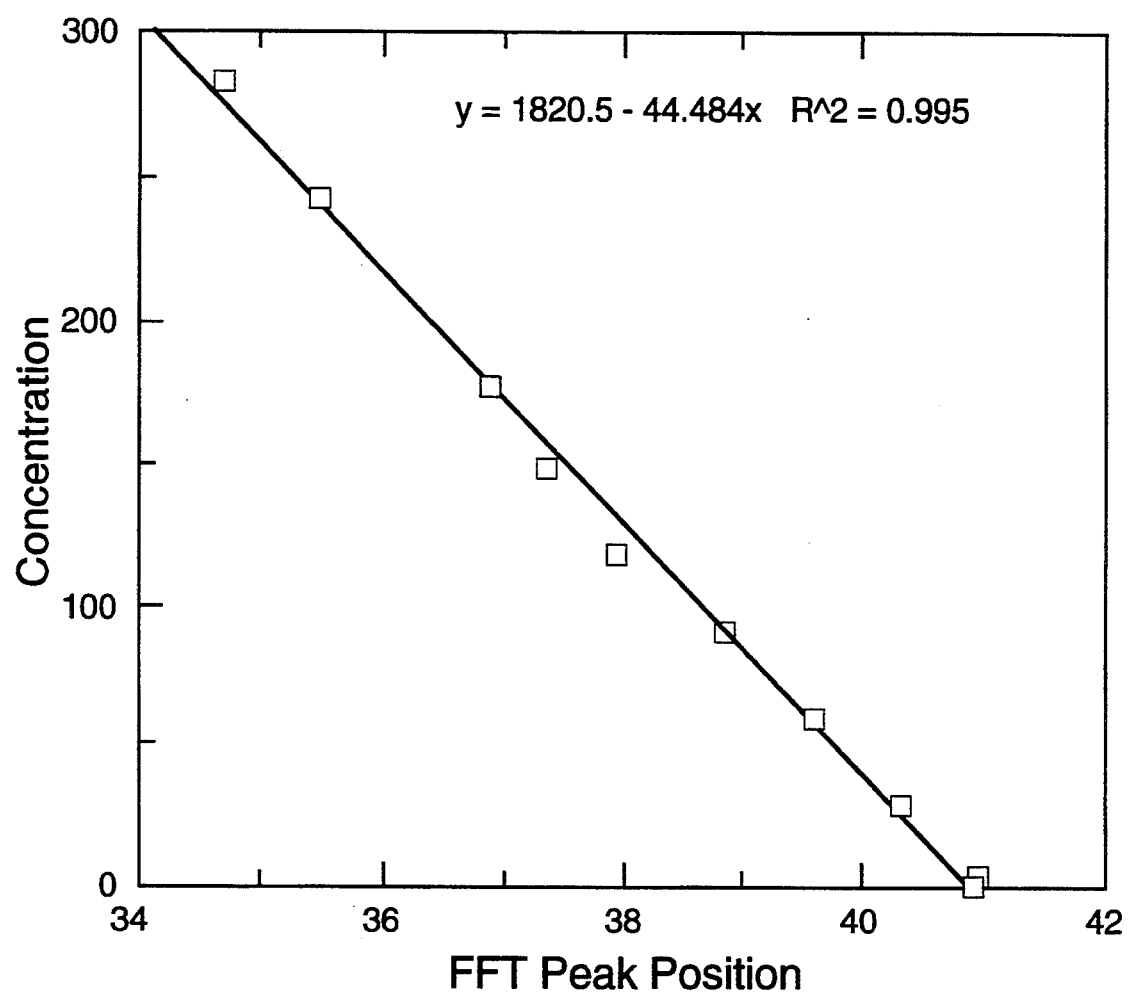
FIG. 5 graphically depicts a calibration curve of NaCl concentration in a distilled water solution in a pipe as a function of the FFT peak value.

Calibration curves were constructed for SG and concentration of the solution of distilled water and salt (NaCl) as a function of the FFT peak value. The calibration curves for SG and salt concentration are shown in FIGS. 4 and 5, respectively, and depict the single-valued relationship between these variables. FIGS. 4 and 5 were then used to determine the SG and molarity of unknown solutions with the results shown in Table A. The molarity was calculated from the measured SG and compared to the molarity as prepared. The largest

TABLE A

| Test Sample Number | SG measured | SG known | SG difference |
|---|---|---|---|
| 1 | 1.1012 | 1.1016 | 0.005 |
| 2 | 1.031 | 1.029 | 0.002 |
| 3 | 1.068 | 1.068 | 0.000 |
| 4 | 1.139 | 1.134 | 0.006 |
| | Molarity measured (g-mol/l) | Molarity known (g-mol/l) | Molarity difference (g-mol/l) |
| 1 | 0.287 | 0.399 | 0.112 |
| 2 | 0.761 | 0.703 | 0.058 |
| 3 | 1.706 | 1.715 | 0.009 |
| 4 | 3.635 | 3.486 | 0.149 | error for these calculations was 0.006 SG over the range of 1.000 to 1.139 SG units and 0.15M over the range 0.399M to 3.635M on Test Sample #4. Accuracy of the 4 samples was 0.18M ($3\sigma$).

Figure 6:
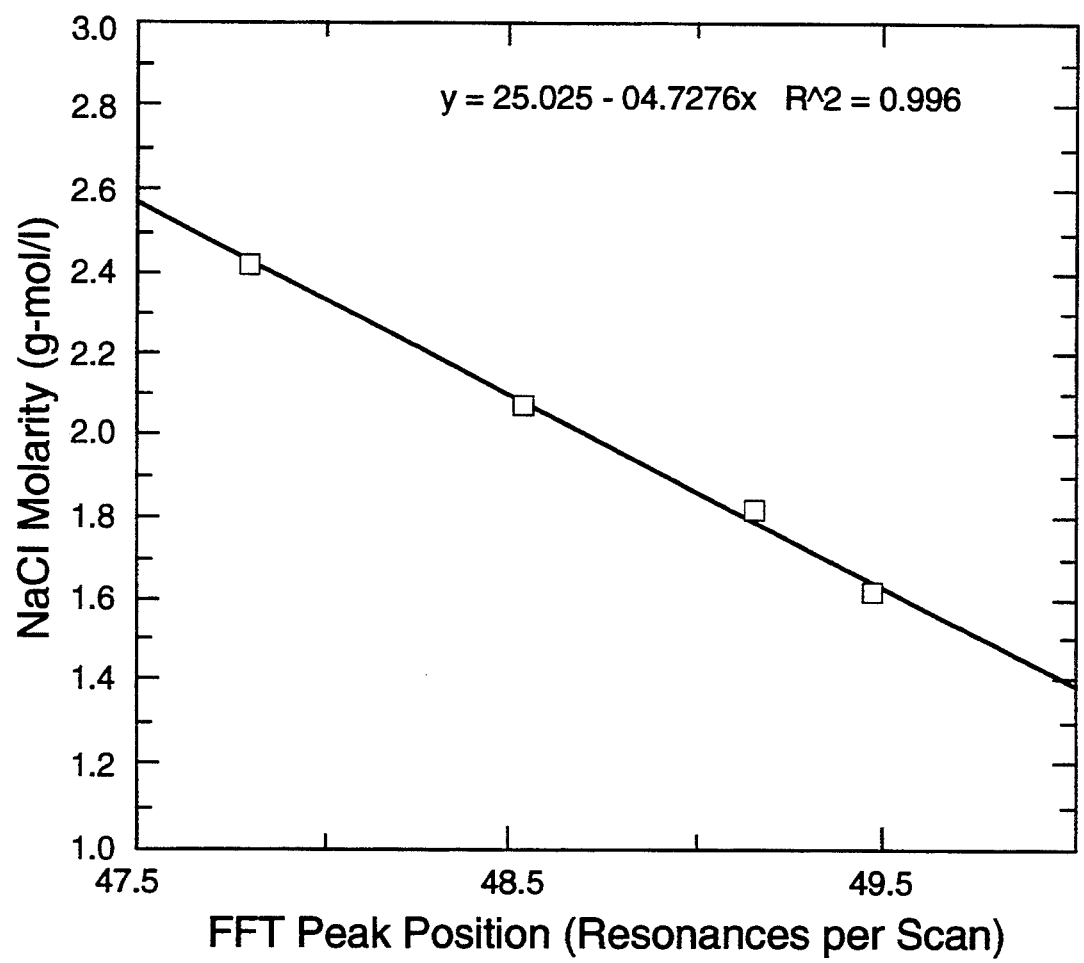
FIG. 6 graphically depicts a calibration curve of NaCl concentration as a function of the FFT peak value using a slab tank to contain the fluid.
Figure 7:
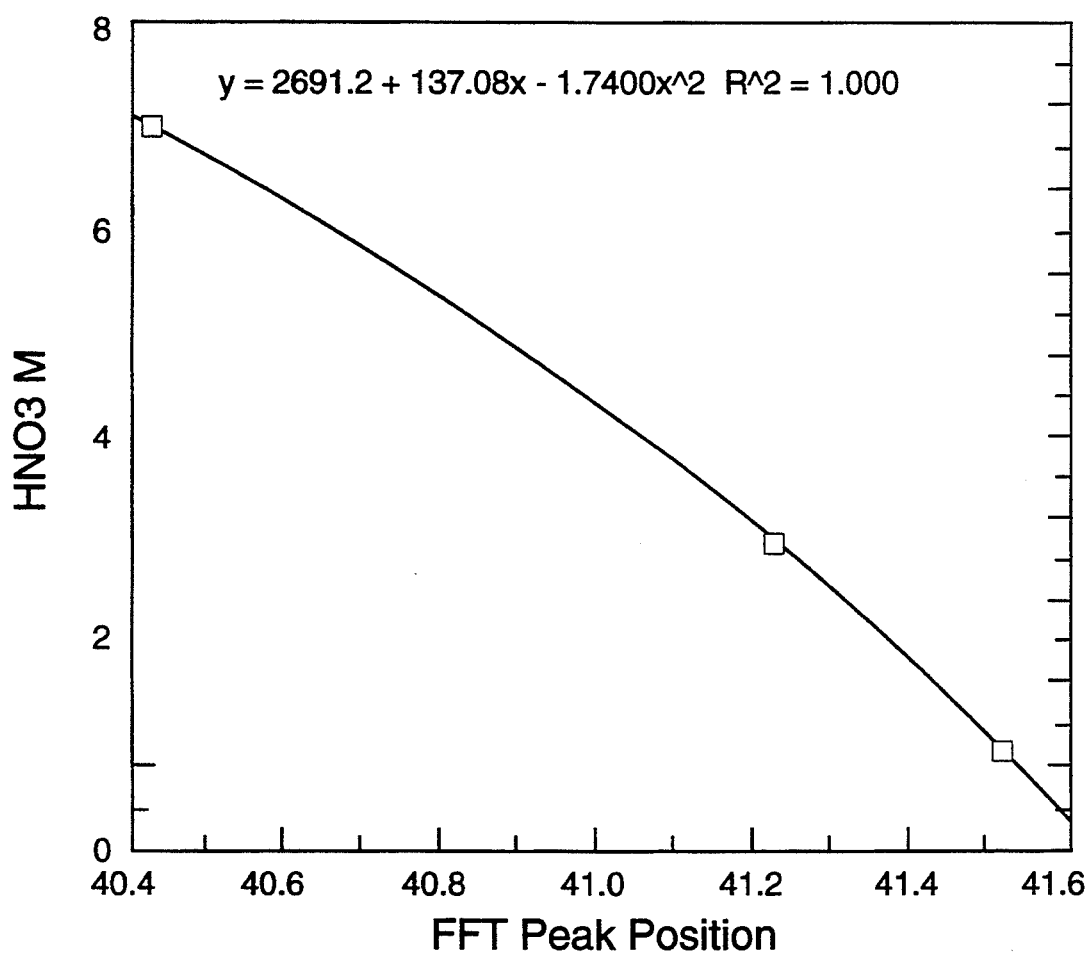
FIG. 7 graphically depicts a calibration curve of nitric acid ($HNO_3$) concentration in a stainless steel pipe.

To illustrate the application of the system to containers other than pipes and solutions other than NaCl, a slab tank was used to contain a NaCl solution and nitric acid was calibrated in $\frac{3}{4}$ inch stainless steel process pipe. FIG. 6 illustrates the linearity of the FFT relationship for a NaCl solution in a slab tank rather than a pipe. FIG. 7 illustrates the sensitivity and single valuedness of the system with nitric acid. Thus, calibration curves can be constructed and solution process SG and concentration parameters can be measured over a variety of solutions and container structures. The noninvasive nature and accuracy of the process for a given geometry provides a highly desirable technique for process control.

The foregoing description of preferred embodiments of the invention have been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for the determination of a process value functionally related to the specific gravity and solute concentration of a process fluid solution located in a selected structure, comprising the steps of:

attaching an excitation transducer and a receiver transducer external to said structure in operable proximity to said process fluid solution;

exciting said fluid solution and said structure over a selected range of frequencies greater than response frequencies of said structure to generate an ultrasonic response spectrum for said fluid solution;

performing a fast fourier transform (FFT) of said response spectrum to output a set of FFT values; and determining the peak value of said FFT from said set of FFT values to output a process value functionally related to said specific gravity and said solute concentration of said process fluid solution.

2. A method according to claim 1, wherein the step of forming said peak value of said FFT includes fitting a curve to said set of FFT values, wherein said peak value of said FFT is determined from said curve.

* * * * *